United States Patent [19]
Gross

[11] Patent Number: 5,587,933
[45] Date of Patent: Dec. 24, 1996

[54] SUPPORT ENHANCING DEVICE AND ASSOCIATED METHOD

[75] Inventor: Clifford M. Gross, Roslyn, N.Y.

[73] Assignee: BCAM International, Inc., Melville, N.Y.

[21] Appl. No.: 340,541

[22] Filed: Nov. 16, 1994

Related U.S. Application Data

[63] Continuation-in-part of Ser. No. 277,230, Jul. 19, 1994.

[51] Int. Cl.$^6$ .............................. A61H 7/00; A61H 1/00; G06F 15/00
[52] U.S. Cl. .............. 364/558; 364/413.01; 364/413.02; 297/284.3; 601/98
[58] Field of Search ...................................... 364/558, 550, 364/554, 551.01, 413.01; 297/284 R, 284.1–284.4, 284.6; 73/12.01, 12.08, 760, 172; 36/136, 132; 601/84–100

[56] References Cited

U.S. PATENT DOCUMENTS

| | | |
|---|---|---|
| 3,866,606 | 2/1975 | Hargest . |
| 3,867,732 | 2/1975 | Morrell . |
| 4,190,286 | 2/1980 | Bentley ................................... 297/284 |
| 4,655,505 | 4/1987 | Kashiwamura et al. ................ 297/284 |
| 4,995,173 | 2/1991 | Spier ........................................ 36/29 |
| 4,999,932 | 3/1991 | Grim ..................................... 36/29 X |
| 5,060,174 | 9/1991 | Gross ..................................... 364/558 |
| 5,170,364 | 12/1992 | Gross et al. ........................... 364/558 |
| 5,176,424 | 1/1993 | Tobita et al. ......................... 297/284.1 |
| 5,283,735 | 2/1994 | Gross et al. ....................... 364/413.02 |
| 5,462,516 | 10/1995 | Anderson . |

OTHER PUBLICATIONS

Gross et al., "Evaluation of an intelligent seat system", Applied Ergonomic, V. 26, N. 2, pp. 109–116 Apr. 1995.

*Primary Examiner*—Ellis B. Ramirez
*Assistant Examiner*—Kamini S. Shah
*Attorney, Agent, or Firm*—Snell & Wilmer L.L.P.

[57] ABSTRACT

A device for supporting a human being comprises a superstructure defining a support surface in contact with a body part of a person and measurement componentry on the superstructure for periodically measuring a predetermined biomechanical parameter of the person's body part to determine a load distribution on the body part. The measurement componentry includes a fluid filled reservoir at the support surface and a pressure detector in operative engagement with fluid in the reservoir for monitoring changes in the pressure of the fluid, due, for example, to varying loads caused by physical activity. Control circuitry is operatively coupled to the pressure detector for monitoring and characterizing changes in pressure of the fluid over time. Form control componentry is disposed on the superstructure and is operatively connected to the measurement componentry for automatically subjecting the support surface, in response to the determined load distribution, to forces tending to modify a contour of the support surface. The form control componentry may include a pressurization source for modifying a base pressure of the reservoir fluid. The control circuitry also controls or operates the form control componentry to periodically alter the forces exerted on the contour so as to provide a cyclic massage to the person's body part.

32 Claims, 5 Drawing Sheets

SUPPORT ENHANCING DEVICE AND ASSOCIATED METHOD

CROSS-REFERENCE TO RELATED APPLICATION

This application is a continuation-in-part of commonly owned application Ser. No. 08/277,230 filed Jul. 19, 1994 now allowed.

BACKGROUND OF THE INVENTION

This invention relates to a device and an associated method for improving the efficacy of a personal support. particularly, this invention relates to a device and an associated method for automatically affecting the form, contour and/or support pressure of a personal support such as an article of clothing, a safety or protective device, or an article of furniture. Even more particularly, this invention relates to a method and associated apparatus for providing an automatically controlled massage.

Automated massage devices, such as vibrating beds and chairs, as well as smaller, hand-held vibrators, have been known for many years. Vibrations are generated by any of several mechanisms, including, for example, motors provided on rotors with eccentrically mounted weights. The vibrations are regular and can be varied generally only as to frequency. Also, it is to be noted that vibration based on massage may contribute to somatic resonance of specific body parts, e.g.,the spine at 5–7 Hz, leading to fluid reduction and increased stress.

A more recent development in the art of automated massage comprises a periodic inflation and deflation of a bladder provided, for example, in the lumbar area of a chair. The bladder inflates and deflates the same amount, regardless of the particular anatomies of the individual users, i.e., regardless of the locations of apexes of spinal curves and curvatures.

Because conventional massage equipment does not account for differences among individuals, massage treatment is not only generally suboptimal but may also exacerbate injuries or introduce deviations leading to organic stresses.

It is to be noted that automated massage systems can be applied not only to support surfaces such as chairs and beds, but can be useful in promoting healing in areas surrounded by personal supports such as therapeutic braces. Athletic equipment, too, can benefit by controlled massage.

Another kind of personal support surface is a bed or a chair. It would be desirable, for instance, to modify the support characteristics of a bed in accordance with the stress or loads experienced by different parts of the user's body, in order to minimize unhealthy stress distributions. Stress on a sleeper's body can be estimated in part by determining the posture of the sleeper. More specifically, a person sleeping on his stomach is apt to require different support than a person lying on his side or his back. Optimally, the rigidity or firmness of different parts of a mattress should be varied depending on the posture of the sleeper.

OBJECTS OF THE INVENTION

An object of the present invention is to provide a method for customizing an automated massage to the anatomy and/or needs of the individual user.

Another object of the present invention is to provide such a method which can be used in conjunction with a technique for optimizing comfort, fit and/or load distribution of surfaces in contact with the human body.

Another, more specific, object of the present invention is to provide such a method which automatically produces an optimal load or pressure distribution and then varies the load or pressure to effect a massage.

A further object of the present invention is to provide a device which automatically implements the method of the invention.

These and other objects of the present invention will be apparent from the drawings and detailed descriptions herein.

SUMMARY OF THE INVENTION

A method for supporting a human being comprises, in accordance with the present invention, the steps of (a) providing a superstructure defining a support surface, (b) placing a body part of a person in contact with the support surface, (c) automatically measuring a predetermined biomechanical parameter of the person's body part, upon engagement of the body part with the support surface, to determine an actual load distribution on the body part, (d) automatically determining an optimal load distribution wherein comfort of the person's body part is maximized according to an empirical regression equation or table, (e) upon completion of the steps of measuring and determining, automatically subjecting the support surface to forces tending to modify a contour of the support surface so as to conform the actual load distribution to the optimal load distribution, and (f) subsequently to the step of subjecting, periodically and automatically altering the forces exerted on the contour so as to provide a cyclic massage to the person's body part.

In a specific embodiment of the present invention, the measured biomechanical parameter is stress, as determined by measuring the pressure in one or more pressure chambers defining the support surface. The actual load distribution is modified by varying the pressures of the different chambers.

The support surface may take the form of one or more panels of a therapeutic brace or a chair back. In the latter case, the step of measuring includes the step of monitoring biomechanical stress on the person's back.

According to another feature of the present invention, altering the forces on the support surface to provide a cyclic massage includes the step of changing the forces so as to separately modify discrete regions of the actual load distribution in a predetermined sequence. This means, for example, that in a chair back, the pressures applied at the pelvic, lumbar, thoracic and neck regions are varied from optimum in a predetermined sequence. Where one or more regions of the support surface are themselves divided into zones, the pressures applied in the zones of any particular region may be temporarily varied from optimum in a preset fashion.

This sequencing of pressure variation is necessarily executed where the pressure chambers are connected via a manifold to a single pressurization source. However, the sequencing may also be performed where each pressure chamber is connected via respective, dedicated tubing and a respective dedicated valve to a pressure source.

According to a more particular feature of the present invention, changing the forces exerted at the support surface includes the step of modifying each of the regions of the actual load distribution according to a respective predetermined multiplier. Thus, in a chair back, the pressures applied at the pelvic, lumbar, thoracic and neck regions may be reduced from respective optimal levels by different fractions.

Generally, it is contemplated that once the optimal load distribution has been attained throughout the support surface, the pressures in one or more regions are reduced slightly from optimum. In a subsequent adjustment, the pressures are returned to their optimal levels, thereby restoring the optimal load distribution. This load distribution may be reformulated or recomputed in accordance with updated measurements of the selected biomechanical parameter (e.g., stress or pressure).

In addition, or alternatively, it is possible to vary the loads in one or more different regions of the load distribution by incrementally increasing the pressures in the different chambers of the support surface. In this case, the pressures may be restricted by pre-established upper limits. Once an upper limit is attained in any one pressure chamber, as measured by periodic sensing, the pressure in that chamber is automatically reduced to the optimal pressure, accordingly to the latest measurement of the respective selected biomechanical parameter.

Where the modification of load or of pressure in the different chambers of the support surface occurs in a predetermined sequence, as preferred, a comfort wave is generated in the support surface. In accordance with the discussion above, a comfort wave can be propagated throughout the entire support surface and/or within different regions of the load distribution or support surface. The comfort waves are generated periodicially or cyclically in accordance with the invention.

According to an additional feature of the present invention, the method further comprises the step of automatically selecting, from among a plurality of predefined regions of the load distribution or, concomitantly, the support surface, a preferred region having a lowest average comfort rating or a highest comfort variability. The load-controlling forces are altered first in the preferred region. Specifically, where the load distribution depends on pressures in a plurality of pressure chambers, the pressure in a chamber corresponding to the preferred region is altered prior to changing the pressures in the other chambers of the support.

According to a further feature of the present invention, the method also comprises the steps of automatically comparing the actual load distribution, region by predefined region, with respective maximum load thresholds. Upon determining that load in any one of the regions has exceeded the respective maximum load threshold, the forces exerted on the support surface in that region are automatically adjusted to reduce the actual load in the region to match the respective maximum load threshold.

According to another feature of the present invention, the method further comprises the steps of automatically measuring a preselected physical parameter at a plurality of locations along the support surface, automatically comparing measured parameter values with preset ranges, and, upon determining that measured value of the parameter in a region of the support surface is outside of a respective preset range, initiating a massage cycle in the region. The monitored physical parameter may be temperature, mechanical shock, or humidity.

A device for supporting a human being comprises, in accordance with the present invention, a superstructure defining a support surface positionable in contact with a body part of a person, and measurement componentry on the superstructure for periodically measuring a predetermined biomechanical parameter of the person's body part to determine a load distribution on the body part. Form control componentry is disposed on the superstructure for automatically subjecting the support surface to forces tending to modify a contour of the support surface. A memory is provided on the superstructure for storing an empirical regression equation or table. A computing unit is operatively connected to the memory, the measurement componentry and the form control componentry for accessing the memory, in response to a load distribution measured by the measurement componentry, to determine an optimal load distribution wherein comfort of the person's body part is maximized according to the empirical regression equation or table. The computing unit operates or activates the form control componentry to subject the support surface to forces tending to modify the contour so as to conform the actual load distribution to the optimal load distribution. The computing unit also controls or operates the form control componentry to periodically alter the forces exerted on the contour so as to provide a cyclic massage to the person's body part.

Pursuant to another feature of the present invention, the measurement componentry includes a plurality of fluid filled reservoirs or chambers at the support surface and at least one pressure detector operatively engageable with fluid in the reservoir. Each reservoir may also be connected to a pressurization assembly of the form control componentry, which is responsive to the computing unit to selectively modify the pressurization levels of the different reservoirs for purposes of conforming the actual load distribution to the optimal load distribution and providing a cyclic massage to the person's body part. Modifying pressures of fluid in the reservoirs serves to alter pressures exerted by the support surface on the body part.

Where the support surface is a chair back, the measurement componentry includes means for monitoring biomechanical stress on the person's back.

According to another feature of the present invention, the device further comprises sensors on the superstructure for automatically measuring a preselected physical parameter at a plurality of locations along the support surface and a comparator disposed on the superstructure and operatively connected to the sensors for automatically comparing measured parameter values with preset ranges. The comparator is operatively connected to the form control componentry for operating that componentry, upon determining that measured value of the parameter in a region of the support surface is outside a respective preset range, to initiate a massage cycle in the region. It is contemplated that the comparator is incorporated in the computing unit.

The sensors may include temperature sensors, mechanical shock sensors, and/or humidity sensors.

A method and an associated apparatus in accordance with the present invention provide a customized automated massage treatment. The technique takes into account different anatomies, as well as variations in temperature, moisture and/or other bioparameters at the body part being massaged.

DETAILED DESCRIPTION

Figure 1:
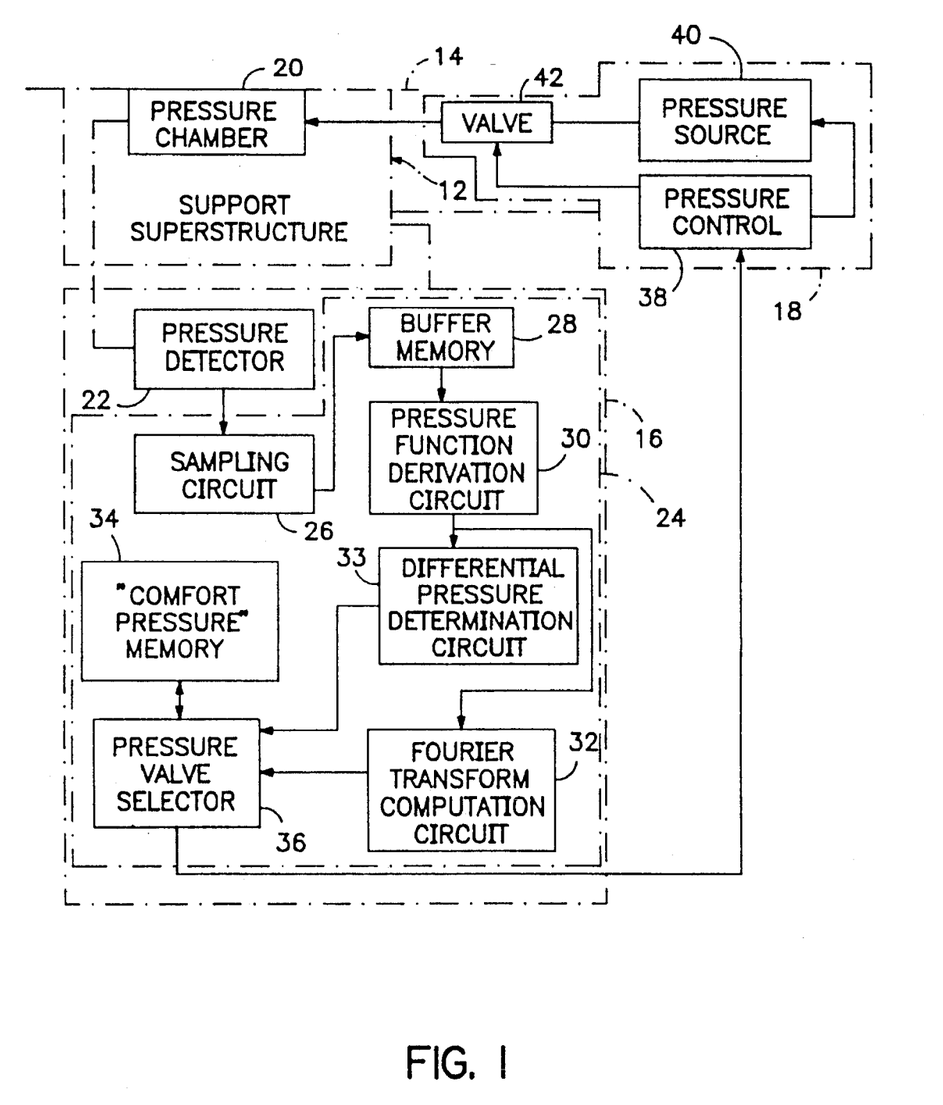
FIG. 1 is a block diagram of a support device for a human being, with automatic pressure or contour control.

As illustrated in FIG. 1, a support device or system for a human being, with automatic pressure or contour control comprises a superstructure, frame, or housing 12 defining a support surface 14 positionable in contact with a body part of a person (not shown). Measurement componentry 16 is provided on superstructure 12 for periodically measuring a predetermined biomechanical parameter, e.g., physical stress, of the person's body part to determine a load distribution on the body part. Form control componentry 18 is disposed on superstructure 12 and is operatively connected to measurement componentry 16 for automatically subjecting support surface 14, in response to the determined load distribution, to forces tending to modify a contour or shape of support surface 14.

Figure 4:
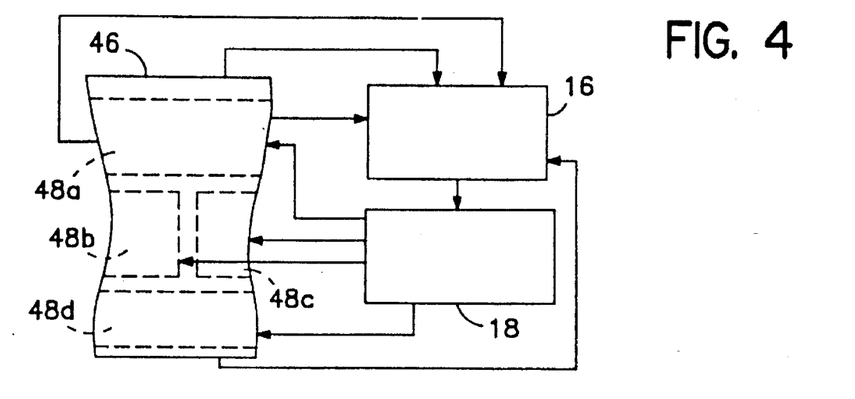
FIG. 4 is a diagram showing another particular embodiment of the device of FIG. 1.

Measurement componentry 16 includes or is connected to a fluid filled reservoir or chamber 20 which is at support surface 14. At least that portion of chamber 20 defined by or adjacent to support surface 14 is partially flexible to enable a modification of the contour or shape of support surface 14. Measurement componentry 16 further includes a pressure detector 22 in operative engagement with fluid in pressure chamber 20 for monitoring changes in the pressure of the fluid, due, for example, to varying loads caused by physical activity of the user or wearer of the support device. In the case of a shoe (FIG. 2), a therapeutic brace (FIG. 4), or a piece of protective athletic padding (NOT SHOWN), the changing physical activity of the user results in different load distributions over time. To satisfactorily handle such applications, measurement componentry 16 includes pressure monitoring circuitry 24 operatively coupled to pressure detector 22 for characterizing changes in pressure of the fluid in pressure chamber 20 over time.

Pressure monitoring circuitry 24 includes a sampling circuit 26 operatively coupled to detector 22 for periodically sampling the fluid pressure in chamber 20, as sensed by detector 22. Sampling circuit 26 is electrically tied to a buffer memory 28 which stores a predetermined number of successive pressure values. Pressure monitoring circuitry 24 further includes a subcircuit 30 linked at an output to buffer memory 28 for deriving measured differential pressure as a function of time.

A second subcircuit 32 of pressure monitoring circuitry 24 operatively connected at an output to subcircuit 30 functions to compute a Fourier Transform on the pressure function determined by subcircuit 30, converting pressure function of time to a spectral (frequency) function. Subcircuit 32 functions in conjunction with another subcircuit 33 of pressure monitoring circuitry 24 operatively tied at an output to subcircuit 30. Subcircuit 33 operates to determine differential pressures associated with spectral frequencies computed by subcircuit 32.

Another subcircuit 34 of pressure monitoring circuitry 24 is a memory which stores a table of optimal comfort pressures as a function of frequency and differential pressure. Subcircuit 34 is accessed by a pressure value selection subcircuit 36 which is operatively connected to Fourier computation subcircuit 32 and determination subcircuit 33 for receiving calculated frequency and pressure data therefrom. In response to that pressure and frequency data, subcircuit 36 selects a "comfort pressure" from the table of such values stored in memory 34.

The comfort pressures stored in memory subcircuit 34 represent optimal pressures for the fluid in chamber 20, i.e., pressures which maximize comfort and support for the wearer, depending on the type and intensity of physical activity and accordingly on the load distribution experienced by the body part in contact with support superstructure 12. Once determined by pressure monitoring circuitry 24, the optimal pressure (the comfort pressure selected from memory 34) is implemented in pressure chamber 20 by form control componentry 18. Componentry 18 includes a pressure control circuit 38 connected at an output to pressure value selector subcircuit 36 and at an input to a pressure source or pressurization element 40 such as a pump. Pressure source 40 is connected to pressure chamber via a valve 42 which is responsive to pressure control 38. Valve 42, which is part of form control componentry 18, is controlled to release pressure fluid from chamber 20 or to admit more fluid into that chamber from pressure source 40, in accordance with control signals from pressure control 38.

The comfort pressures stored in memory subcircuit 34 are determined empirically. A series of test individuals are subjected to each of a plurality of different load distributions over time and to a plurality of different test pressures at the respective support surface for each load distribution. The subjects are asked to select which test pressure is most comfortable. A statistical mean, median or mode is computed from the selected test pressures. That mean, median or mode is designated the comfort pressure for the respective load distribution.

As an alternative technique to tabular comfort data storage and access, subcircuit 36 may compute a comfort pressure from the calculated frequency and pressure data from subcircuits 32 and 33 by utilizing a multiple regression equation whose coefficients are empirically determined and stored, e.g., in memory subcircuit 34. The exact values of the coefficients will vary depending on the number of test subjects and their responses.

Figure 7:
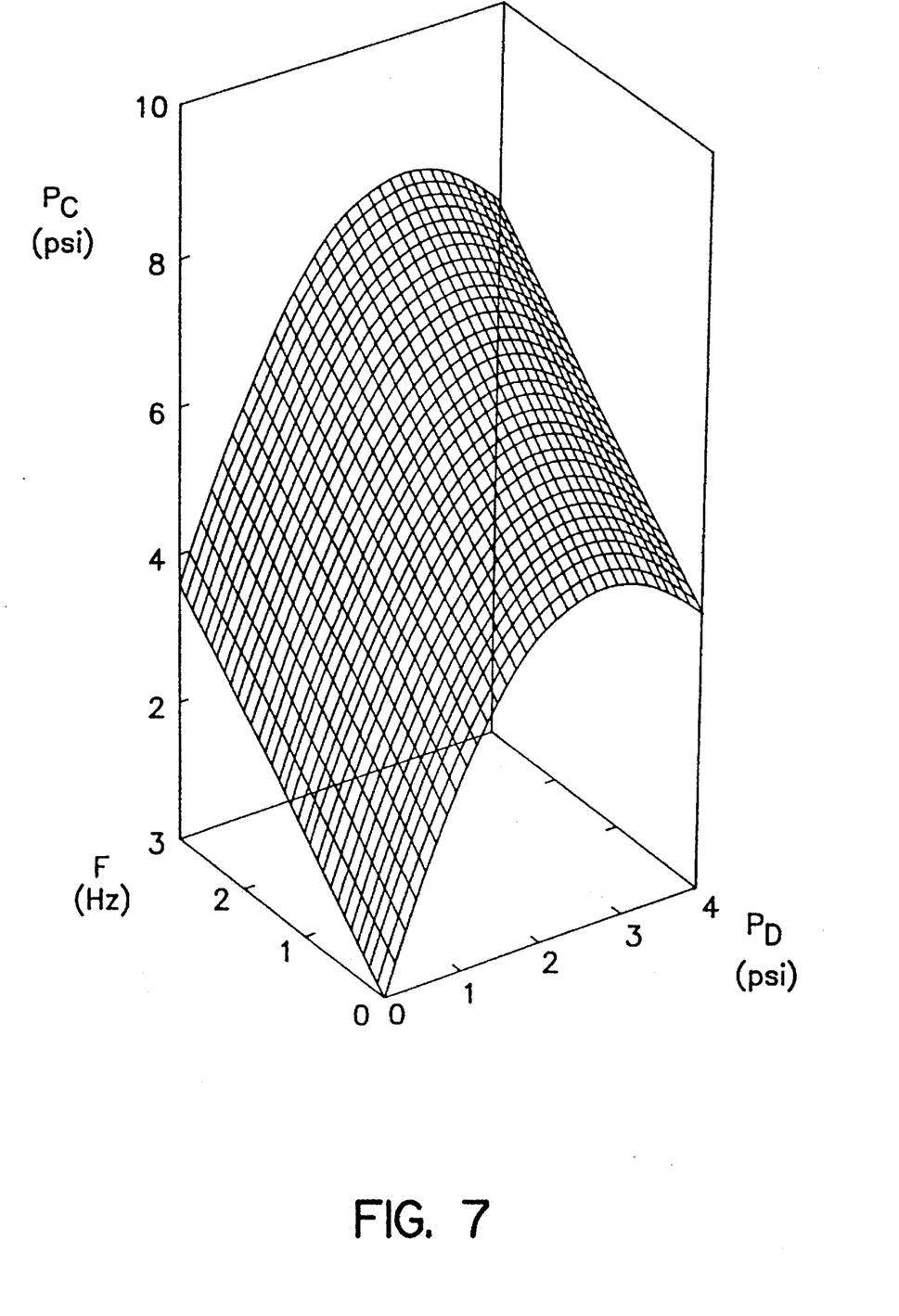
FIG. 7 is a graph showing comfort pressures of a bladder or pressure chamber in an athletic shoe as a function of frequency and differential pressure as computed via a Fourier Transform.

FIG. 7 is a graph showing comfort pressures $P_C$ of a bladder or pressure chamber in an athletic shoe as a function of frequency F and differential pressure PD as computed via a Fourier Transform. The graph of FIG. 7 is derived using the following multiple regression equation as a model:

$$P_C = -0.57 \times (P_D)^2 + 3.22 \times P_D + 1.18 \times F.$$

In the model significance test for this illustrative multiple regression equation, $p < 0.0001$, while $R^2 = 0.89$.

Figure 2:
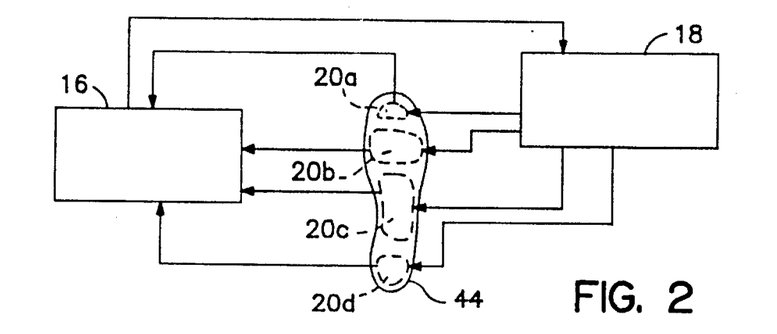
FIG. 2 is a diagram showing a particular embodiment of the device of FIG. 1.

FIG. 2 schematically depicts a particular embodiment of the device of FIG. 1 where superstructure 12 takes the form of an athletic shoe 44. Support surface 14 may in that case take the form of an insole (not shown) of shoe 44. Pressure chamber 20 is one of a plurality of pressure chambers 20a, 20b, 20c, 20d disposed under different areas of the sole, namely, the toe, the balls, the instep, and the heel, respectively. Pressure chambers 20a, 20b, 20c, 20d are operatively connected to sampling circuit 26 of measurement componentry 16 via one or more detectors 22 (not shown) and pressure source 40 of form control componentry 18 via value 42. In this case, sampling circuit 26 sequentially samples the pressures of the different chambers 20a, 20b, 20c, 20d, while subcircuit 30 determines four different functions of pressure vs. time. Subcircuit 32 performs a Fourier Transform computation for each of the pressure functions, while subcircuit 36 selects four comfort pressures based on the results of the Fourier Transform. In response to pressure control 38, valve 42 and pressure source 40 function to institute the selected comfort pressures in the respective chambers 20a, 20b, 20c, 20d of shoe 44.

In the case of shoe 44, measurement componentry 16 effectively determines the frequency and magnitude of impacts on the user's foot. In response to this determination, form control componentry 18 modifies the base pressures in chambers 20a, 20b, 20c, 20d to optimize comfort for the user. Thus, the pressures applied to the fluid in chambers 20a, 20b, 20c, 20d where the user jumps frequently as in basketball or volleyball will be different from the pressures applied to the fluid in chambers 20a, 20b, 20c, 20d where the user has a lesser, more constant impact on the foot as in field and track activities.

The method of operation of the device of FIG. 1 as applied to an athletic shoe will enable adaptation of the shoe pressure chambers 20a, 20b, 20c, 20d to different ranges of activity even during the same exercise or competition. Accordingly, during a tennis match, pressure monitoring circuitry 24 can detect a change in tactics from a consistent base line volleying to a frequent rush to the net and induce form control componentry 18 to modify the pressure in chambers 20a, 20b, 20c, 20d accordingly. This capability arises from the monitoring of pressure changes over time and the automatic analysis of those pressure changes to provide an optimal comfort pressure.

In the embodiment of FIG. 2, a single pressure detector 22 (not shown) may be operatively connected to the different pressure chambers 20a, 20b, 20c, 20d. Alternatively, multiple pressure detectors may be provided. In another alternative system, pressure detector 22 may be operative to sample sequential of measurement componentry 16 via one or more detectors 22 (not shown) pressures from only one chamber 20a, 20b, 20c, or 20d which is then used as the standard by which the comfort pressures of the other chambers are set. It is to be noted that, for a shoe or other similar pressurizable support, the "comfort pressure" becomes a minimum or base pressure relative to which changes of pressure or differential pressures are indicative of load or stress on the foot or other body part which is in contact with the support.

In alternative specific applications or embodiments, support surface 14 may be substantially the entire insole of an shoe, a side panel, an upper, or in the case of a high topped shoe, an ankle portion.

Figure 3:
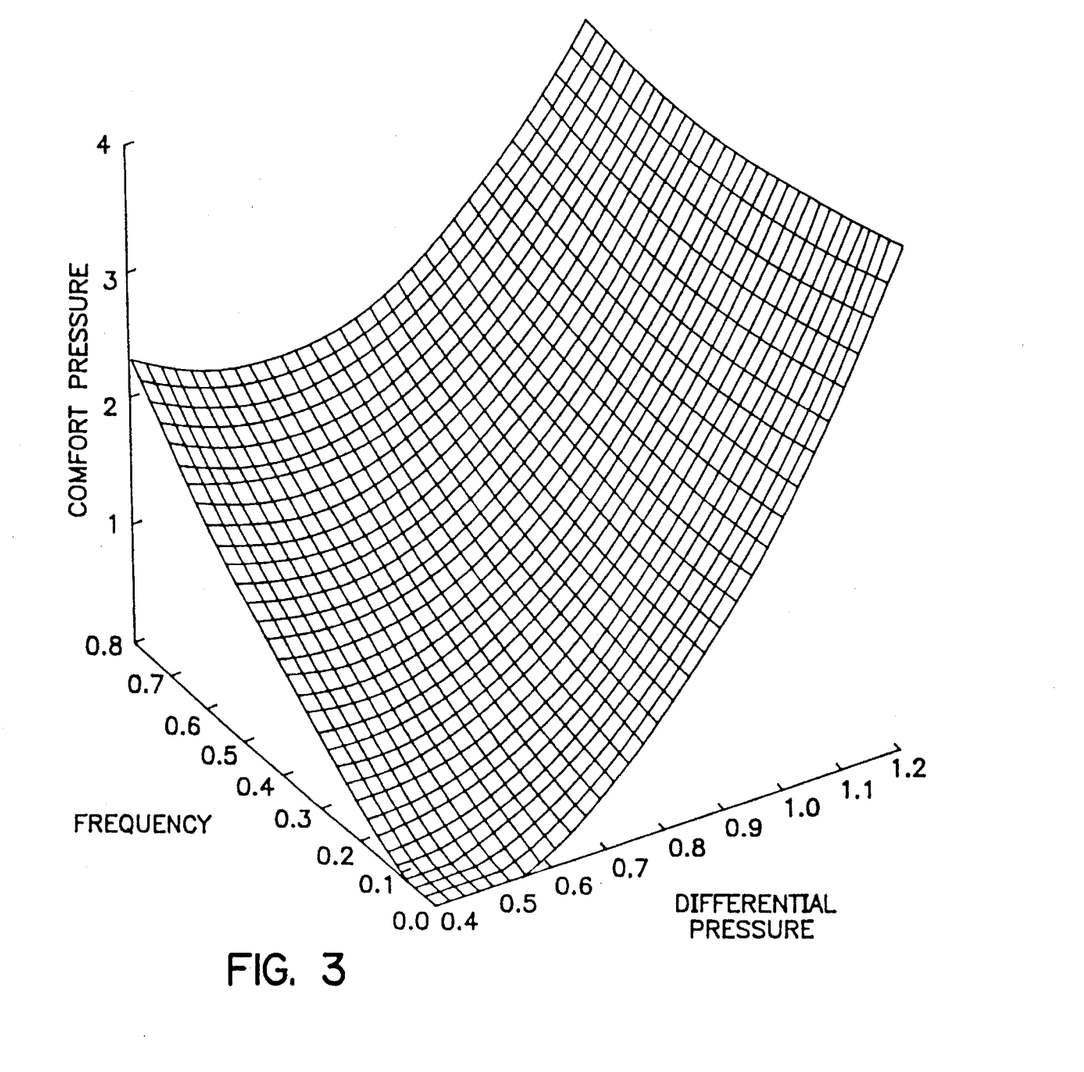
FIG. 3 is a graph showing comfort pressures of a pressurizable or conformable support surface as a function of frequency and differential pressure as computed via a Fourier Transform.

FIG. 3 is a graph illustrating, by way of example, a mathematical comfort surface. With an arbitray scale, the z-axis represents an emirically determined comfort pressure as a function of an impact frequency and magnitude as determined via Fourier Transform. The information represented by the graph of FIG. 3 is encoded in tabular form and stored in memory 34.

Where a Fourier Transform computation results in a plurality of frequency and magnitude points, selection subcircuit 36 may operate to select a comfort pressure based on a categorization of the results. Such categories may be predefined, for example, in accordance with the particular applications intended for the support. For an athletic shoe, relevant classifications may include (a) low impact, high frequency impacts, (b) high impact, low frequency, (c) high impact, high frequency, and (d) low impact, low frequency. Upon an analysis of transform results to determine the category, selector subcircuit 36 accesses memory 34 to determine optimal pressurization.

Where support superstructure 12 (FIG. 1) is a protective athletic device such as a shoe 44 (FIG. 2), a knee brace 46 (FIG. 4), or a shoulder pad (not shown), measurement componentry 16 advantageously functions to monitor frequency and intensity of impacts. The effect of therapeutic braces is also improved or optimized where measurement componentry 16 is provided for monitoring frequency and intensity of impacts on the braced body part. For example, the degree of pressure applied to knee or leg brace 46 (FIG. 4), and thus the tightness of the fit of the brace to the knee or leg, can be reduced where the individual is resting or walking slowly, to permit slow strengthening of the leg muscles. In contrast, when the individual is running or jumping, the degree of pressure applied to a knee or leg via pressure chambers 48a, 48b, 48c, 48d in brace 46, and thus the tightness of the fit of the brace to the knee or leg, can be increased to provide greater support. It is also possible to program form control componentry 18 so that the degree of support provided varies over time. As healing progresses, less support is applied even in stressful activities such as running or jumping.

Figure 5:
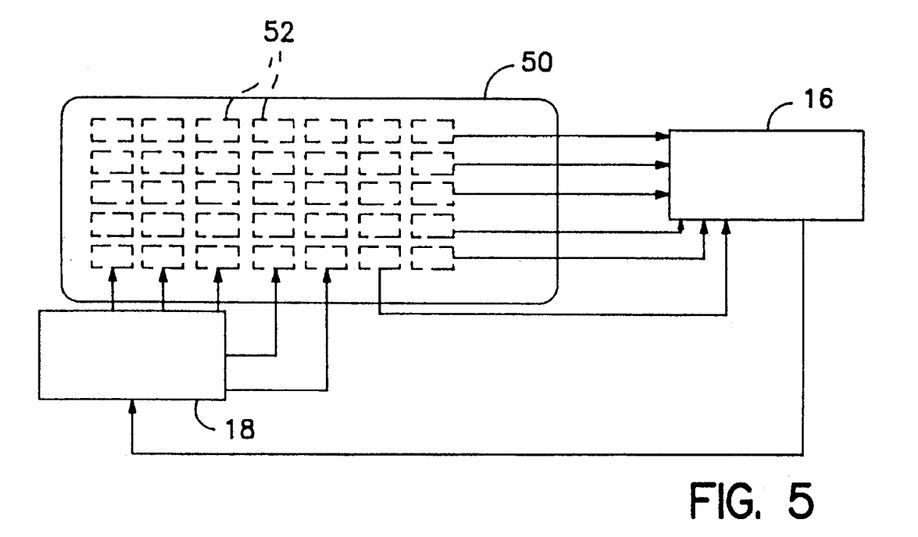
FIG. 5 is a diagram showing a further particular embodiment of the device of FIG. 1.

FIG. 5 depicts a bed 50 provided with a plurality of relatively small pressurizable chambers 52 disposed in a rectangular array. Chambers 52 are operatively connected to pressure sampling circuit 26 of measurement componentry 16 via one pressure detector or, alternatively, respective detectors and to pressure source 40 of form control componentry 18 via valving (not shown). In the case of bed 50, it is in many instances not so important to measure changes over time, but to determine whether a change in posture has occurred and to determine the new posture for purposes of modifying the pressurization of chambers 52 to maximize comfort.

During steady state operation of the system of FIG. 5, the inputs from pressure chambers 52 are monitored to detect any change in loading. Once a change in loading has occurred, the differential pressures are compared to pre-established load distributions which have been stored in an internal memory. This comparison results in a determination of the new loading, i.e., the new posture assumed by the person on the bed. Upon determining the new posture, a memory of comfort pressure distributions is consulted to ascertain a most comfortable pressure distribution, as determined empirically. Pressure source 40 and its associated valving is then actuated to implement the optimal load distribution.

In the case of bed 50, form control componentry 18 actually modifies a contour of bed 50. Bed 50 conforms at least partially to the profile of the user in contact with the bed. When a user turns to lie on his or her back, the bed changes contour to insert a hump into the hollow of the lower back and to slightly prop up the head. If the user changes to a stomach-down position, form control componentry 18 modifies the contour of the bed surface to slightly reduce the elevation of the head and to receive a protruding belly or lower abdomen, thereby relieving possible stress on the lower back.

Figure 6:
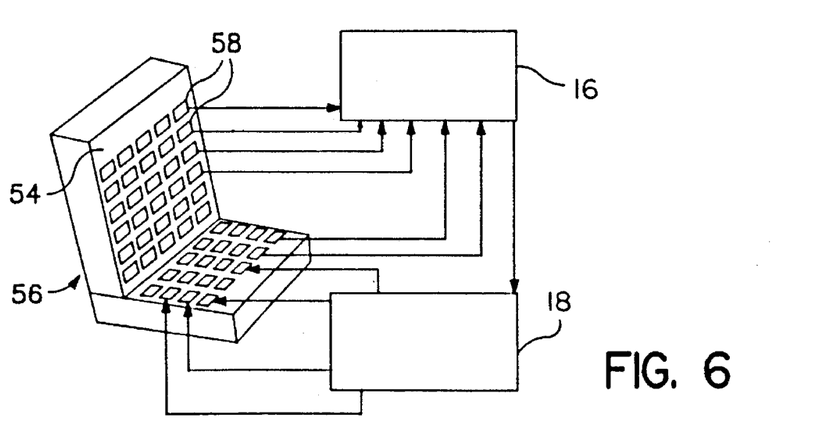
FIG. 6 is a diagram showing yet another particular embodiment of the device of FIG. 1.

FIG. 6 shows support surface 14 as a back 54 of a chair 56. In this case, pressure monitoring circuitry 24 of measurement componentry 16 monitors, in part, biomechanical stress on the user's back as sensed via pressure chambers 58.

In an alternative mode of operation of form control componentry 18 for a bed or chair, the base pressures of an array of pressure chambers are controlled to stimulate desirable motion of the user. In contrast to conventional mechanical beds where the user passively experiences a massage, a bed or chair may be controlled so as to induce desirable movement of the user. Thus, during a night's sleep, a person may be induced, through intelligent control componentry, to move through a prescribed series of positions empirically determined to optimize comfort, relaxation and sleep.

The techniques and devices described herein may be used to study the effects of a physical activity on a human body. Thus, measurement componentry 16, in periodically and automatically measuring physical stress of a body part in contact with support surface 14 and in automatically analyzing physical stress to obtain a distribution of the measured stress, provides useful information to biomechanical investigators researching the reactions of human tissue and organs to differing kinds and levels of physical loading.

Figure 8:
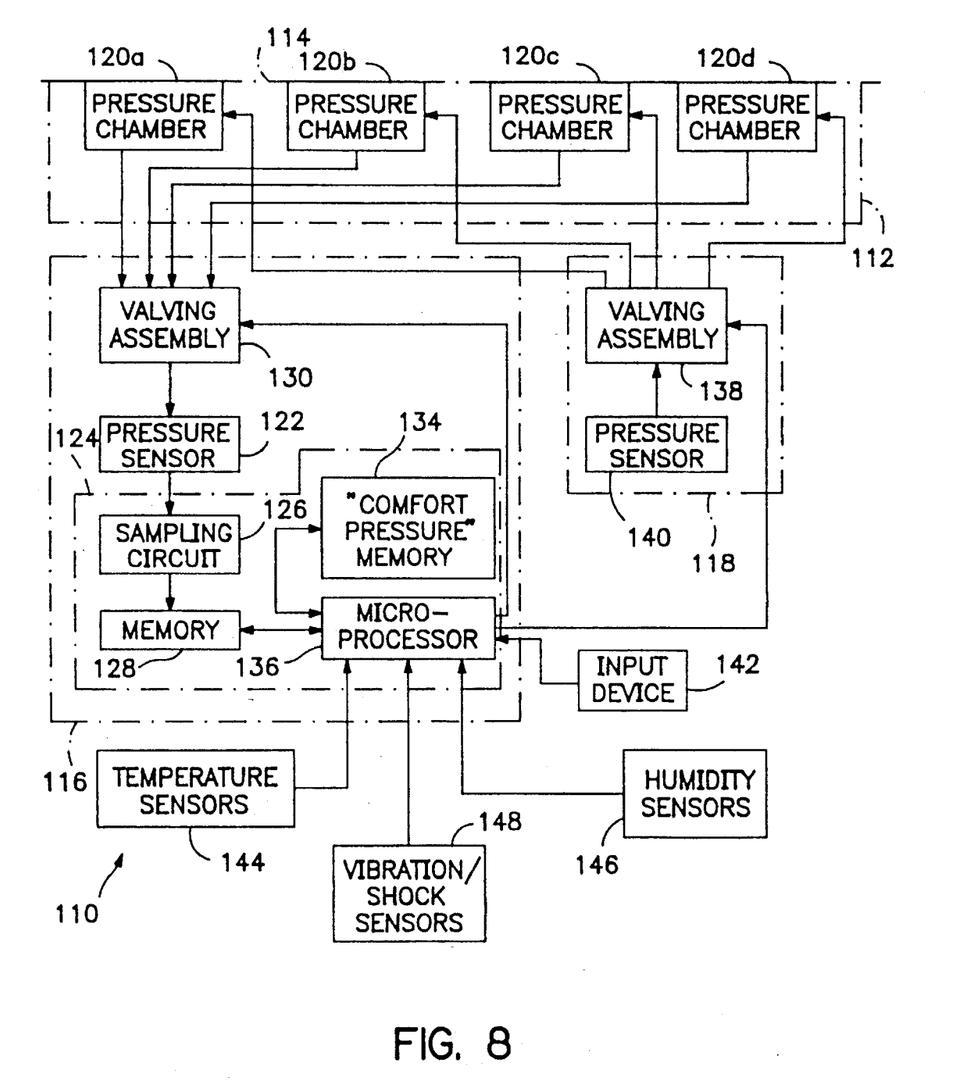
FIG. 8 is a block diagram of another support device for a human being, with automatic pressure or contour control and an automatic massage function in accordance with the present invention.

As illustrated in FIG. 8, a customized support and massage device or system 110 for a human being, with automatic pressure or contour control comprises a superstructure, frame, or housing 112 defining a support surface 114 positionable in contact with a body part of a person (not shown). Measurement componentry 116 is provided on superstructure 112 for periodically measuring a predetermined biomechanical parameter, e.g., physical stress or gravitational load, of the person's body part to determine a load distribution on the body part. Form control componentry 118 is disposed on superstructure 112 and is operatively connected to measurement componentry 116 for automatically subjecting support surface 114, in response to the determined load distribution, to forces tending to modify a contour or shape of support surface 114.

Support surface 114 exemplarily takes the form of one or more panels of a therapeutic brace or a chair back. In the latter case, the step of measuring includes the step of monitoring biomechanical stress on the person's back.

Measurement componentry 116 includes or is connected to a plurality of fluid filled reservoirs or chambers 120a, 120b, 120c, 120d which are located at or in operative engagement with support surface 114. At least that portion of each chamber 120a, 120b, 120c, 120d defined by or adjacent to support surface 114 is partially flexible to enable a modification of the contour or shape of support surface 114. Measurement componentry 116 further includes a pressure sensor 122 which is operatively connectable separately to pressure chambers 120a, 120b, 120c, 120d via a multiplexing or valving assembly 130. Sensor 122 detects changes in the pressures of the fluid in chambers 120a, 120b, 120c, 120d, due, for example, to varying loads caused by the user or wearer of the support device.

Pressure monitoring circuitry 124 in measurement componentry 116 includes a sampling circuit 126 operatively coupled to sensor 122 for periodically sampling the fluid pressure in chambers 120a, 120b, 120c, 120d, as sensed by sensor 122. Sampling circuit 126 is electrically tied to a buffer memory 128 which stores measured pressure values for the different chambers 120a, 120b, 120c, 120d.

Another subcircuit 134 of pressure monitoring circuitry 124 is a memory which stores a table of optimal comfort pressures for different zones of support surface 114 corresponding to the different pressure chambers 120a, 120b, 120c, 120d. Subcircuit 134 is accessed by a microprocessor or computing unit 136 which is also operatively connected to buffer memory 128 and valving assembly 130. Through selective activation of valving assembly 130, microprocessor 136 controls the connection of pressure chambers 120a, 120b, 120c, 120d to sensor 122, thereby determining a sequence in which pressure values are loaded into memory 128.

Upon the loading of a complete set of pressure values into memory 128, microprocessor 136 determines which pressure chambers 120a, 120b, 120c, 120d correspond to which areas of the user's anatomy. This procedure enables customization of the support and massage device to different users. The matching of chambers 120a, 120b, 120c, 120d to the different anatomical areas of the user is made by analyzing the distribution of load across the different pressure chambers 120a, 120b, 120c, 120d.

Upon determining the correspondence between pressure chambers 120a, 120b, 120c, 120d and the user, microprocessor 136 optimizes load or maximizes comfort by consulting the table of comfort pressures in memory 134. As described in U.S. Pat. Nos. 5,170,364 and 5,283,735, the disclosures of which are hereby incorporated by reference, microprocessor 136 compares the fraction of total load exerted on each of the pressure chambers 120a, 120b, 120c, 120d with a desired range for the respective area of the user's anatomy. In the event that the fraction of total load for any anatomical area is not within the respective desired, microprocessor 136 operates a valving assembly 138 of form control componentry 118 to connect a pressure source or pump 140 (or the atmosphere) to the pressure chamber 120a, 120b, 120c, or 120d corresponding to the particular anatomical area. The resulting change in pressure of chamber 120a, 120b, 120c, or 120d serves to change the shape of load bearing surface 114 to bring the fraction of the total load for the respective chamber within the desired range and to maximize comfort to the user.

As discussed in U.S. Pat. Nos. 5,170,364 and 5,283,735, the comfort pressures stored in memory subcircuit 134 represent optimal pressures for the fluid in chambers 120a, 120b, 120c, 120d, which maximize comfort and support for the wearer. The comfort pressures stored in memory subcircuit 134 are determined empirically. A series of test individuals are subjected to each of a plurality of different load distributions over time and to a plurality of different test pressures at the respective support surface for each load distribution. The subjects are asked to select which test pressure is most comfortable. A statistical mean, median or mode is computed from the selected test pressures. That mean, median or mode is designated the comfort pressure for the respective load distribution.

As an alternative technique to tabular comfort data storage and access, microprocessor 136 may compute a comfort pressure by utilizing a multiple regression equation whose coefficients are empirically determined and stored, e.g., in memory subcircuit 134. The exact values of the coefficients will vary depending on the number of test subjects and their responses.

Upon an optimization of load at surface 114, microprocessor 136 may initiate, in response to instructions from the user via an input device 142 such as a switch or keypad, an automated massage procedure wherein the forces exerted on contour or surface 114 are periodically and automatically altered so as to provide a cyclic massage to the user' body part which is in contact with surface 114. More specifically, microprocessor 136 operates valving assembly 138 to separately modify discrete regions of the actual load distribution in a predetermined sequence. In a chair back, for example, the pressures applied at the pelvic, lumbar, thoracic and neck regions are varied from the established optimum in a predetermined sequence. Of course, one or more regions of support surface 114 may themselves be divided into zones, each zone corresponding to or being defined by one or more respective pressure chambers 120a, 120b, 120c, 120d, etc. Within any one region or support surface 114, the pressures applied in the zones may be temporarily varied from optimum in a preset fashion.

In executing a massage action, microprocessor 136 operates valving assembly 138 to vary the pressures in chambers 120a, 120b, 120c, 120d in a predetermined sequence. The pressures are reduced or increased from optimum values by predetermined amounts or in accordance with predetermined proportions. For example, to effect a massage of a user's back, the pressure or load exerted on the lumbar area may be slightly decreased and the pressures or loads exerted on the pelvis and the thorasic areas slightly increased, by respective preestablished fractions or multipliers. Such a variation in the load distribution across support surface 114 provides a particular kind of massage to the user, with a generally foreseeable and controllable effect on the spinal muscles and spinal column, as well as the other parts of the back.

Alternatively, a massage action induced by microprocessor 136 may comprise the sequential reduction (or increase) of pressure in a series of chambers 120a, 120b, 120c, 120d, each chamber being returned to the respective optimal pressure prior to the reduction (or increase) in pressure of the succeeding chamber. This procedure produces a wave-like massage, where a pressure type wave moves across the support surface, with a timing controlled by microprocessor 136. The amounts or fractions of pressure reduction or increase, as well as the durations of pressure variations and the intervals between pressure modification in the different chambers 120a, 120b, 120c, 120d, may be optimized by empirical studies, with the results stored in memory subcircuit 134.

Sequencing of pressure variation is necessarily executed where pressure chambers 120a, 120b, 120c, 120d are connected via a manifold such as valving assembly 138 to a single pressurization source 140. Such sequencing can, of course, also be performed where each pressure chamber 120a, 120b, 120c, 120d is connected via respective, dedicated tubing and a respective dedicated valve (not shown) to a pressure source (not shown).

In another variation of the massage technique described above, the pressures in chambers 120a, 120b, 120c, 120d may be reduced (or increased) by respective fractions or multipliers and maintained at the respective modified levels until the pressures in all of the chambers 120a, 120b, 120c, 120d have been modified. Subsequently, the pressures in the chambers are returned to the respective levels of the optimum load distribution in a predetermined sequence. This particular procedure also results in a massage wave applied to the user at the support surface 114.

It is to be noted that the massage may be effectuated through a number of successive cycles. Microprocessor 136 periodically checks the load, upon return thereof to the optimum distribution, in order to ensure that the support surface 114 maintains a contour of maximized comfort. Such checks include a comparison of measured loads with the comfort pressures stored in memory subcircuit 134.

Microprocessor 136 also monitors the load during the massage cycles to ensure that undue stressing of the user is not occurring. For example, where the loads in one or more different regions of support surface 114 are varied by incrementally increasing the pressures in the different chambers of the support surface, the pressures in chambers 120a, 120b, 120c, 120d are restricted by pre-established upper limits. Once an upper limit is attained in any one pressure chamber 120a, 120b, 120c, or 120d, as measured by periodic sensing by microprocessor 136, the pressure in that chamber 120a, 120b, 120c, or 120d is automatically reduced to the optimal pressure, accordingly to the latest measurement of the respective selected biomechanical parameter.

Memory 128 may contain two sets of loads or pressure measurements for each chamber 120a, 120b, 120c, and 120d. One pressure measurement corresponds to the last optimum pressure, the other to the instantaneous pressure, including variations induced during a current massage cycle. The pressures may be measured simultaneously with or immediately after connection of pressure source 140 (or the atmosphere) to a particular pressure chamber 120a, 120b, 120c, 120d via valving assembly 138.

Microprocessor 136 automatically selects, from among a plurality of predefined regions of the load distribution or, concomitantly, support surface 114, a preferred region having a lowest average comfort rating or a highest comfort variability. The load-controlling forces are altered first in the preferred region, i.e., the pressure in a corresponding chamber or chambers 120a, 120b, 120c, 120d is modified first.

As discussed above, microprocessor 136 automatically compares the actual load distribution, region by predefined region, or pressure chamber by pressure chamber 120a, 120b, 120c, 120d, with respective maximum load thresholds. Upon determining that load in any one chamber 120a, 120b, 120c, or 120d has exceeded the respective maximum load threshold, the pressure in that chamber is automatically adjusted to reduce the actual load in the region to match the respective maximum load threshold.

As further illustrated in FIG. 8, microprocessor 136 may receive input from a plurality of temperature sensors 144 which are juxtaposed to support surface 114 and distributed therealong. Additionally, humidity or moisture sensors 146 and vibration or shock sensors 148 disposed along surface 114 may provide input to microprocessor 136. In accordance with that input, microprocessor 136 modifies a massage action, for example, to concentrate on an area with a temperature below a certain threshold. The temperature thresholds, stored in memory subcircuit 134, are determined empirically and may vary across the different anatomical areas of a respective subject body part such as the back, or the leg.

Where temperature or moisture is too high, increased massage action may be indicated. High temperature or moisture may indicate tense muscles, for example.

Upon receiving signals from sensors 144, 146, and 148, microprocessor 136, acting as a comparator, consults memory subcircuit 134 to automatically compare the measured parameter values with preset ranges. Upon determining that a measured value of temperature, humidity or shock in a given region of support surface 114 is outside of a respective preset range, microprocessor 136 initiates a massage cycle in and/or around that region.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that pressure or contour control at the contact surface may be implemented in at least some applications by means other than hydraulic or pneumatic. Multiple electric motors operating respective rack and pinion mechanisms may accomplish surface control.

In addition, other kinds of biomechanical parameters may be measured to determine loading of a body part. For instance, local galvanic skin response as an indicator of muscle exertion.

It is to be further noted that mathematical techniques other than the Fourier Transform may be used to characterize or categorize types of motion for purposes of optimizing comfort, fit, and load distribution of surfaces which come into contact with the body. For instance, after a digital filtering to remove spurious peaks, relative or local load peaks are detected by deriving and analyzing first and second derivatives of a pressure function as dervied by subcircuit 30. The load peaks are automatically correlated with the respective pressure magnitudes to determine load distributions. The load distributions are then classified according to the number of peaks of different magnitudes within an arbitrary time period. A load distribution thus measured can be matched with a pre-determined load category and thereby paired with a respective empirically determined comfort pressure.

Accordingly, it is to be understood that the drawings and descriptions herein are proffered by way of example to facilitate comprehension of the invention and should not be construed to limit the scope thereof.

What is claimed is:

1. A method for supporting an animate object, comprising the steps of:
   (a) providing a structure defining a configurable contoured support surface;
   (b) placing a part of the object in contact with said support surface;
   (c) automatically measuring an input parameter to determine a pressure distribution on the part of the animate object in contact with the support structure;
   (d) automatically determining an optimal pressure distribution wherein comfort of the object's part is maximized according to an empirical regression equation or table;
   (e) automatically subjecting said support surface, in response to the selected optimal comfort pressure, to forces tending to modify a contour of said support surface; and
   (f) periodically and automatically altering said forces exerted on said support surface so as to provide a cyclic massage to the object's part.

2. The method defined in claim 1 wherein step (f) includes the step of changing said forces so as to separately modify discrete regions of said actual pressure distribution in a predetermined sequence.

3. The method defined in claim 2 wherein said step of changing includes the step of modifying each of said regions of said actual pressure distribution according to a respective predetermined multiplier.

4. The method defined in claim 1, further comprising the step of:
   (g) automatically selecting, from among a plurality of predefined regions of said pressure distribution, a preferred region having a lowest average comfort rating or a highest comfort variability, said step (f) including the step of altering forces in said preferred region prior to altering forces in others of said regions.

5. The method defined in claim 1, further comprising the steps of:

(g) automatically comparing said actual pressure distribution, in each of a plurality of discrete regions, with respective maximum pressure thresholds; and
   (h) upon determining that pressure in any one of said discrete regions has exceeded the respective maximum pressure threshold, automatically adjusting forces exerted on said support surface in said one of said regions to reduce the actual pressure in said one of said regions to match the respective maximum pressure threshold.

6. The method defined in claim 5 wherein steps (c) and (e) are performed periodically.

7. The method defined in claim 1, further comprising the steps of:
   (g) automatically measuring a preselected input parameter at a plurality of locations along said support surface;
   (h) automatically comparing said measured parameter values with preset ranges; and
   (i) upon determining that said measured value of said parameter in a region of said support surface is outside of a respective preset range, initiating a massage cycle in said region.

8. The method defined in claim 7 wherein step (g) comprises measuring a preselected parameter, wherein said parameter is taken from a group including temperature, mechanical shock, humidity, muscle tension, time and combinations thereof.

9. The method defined in claim 1 wherein a fluid filled reservoir is provided at said support surface and is coupled with said structure, said step (c) including the step of detecting pressure of said fluid in said reservoir.

10. The method defined in claim 9 wherein said step (e) includes the step of modifying the pressure of said fluid.

11. The method defined in claim 1 wherein a fluid filled reservoir is provided at said support surface and is coupled with said structure, said step (e) including the step of modifying the pressure of said fluid, thereby altering pressure exerted by said support surface on said body part.

12. The method defined in claim 1 wherein said support surface is a chair back and said step (c) includes the step of monitoring biomechanical stress on a person's back.

13. The method defined in claim 1 wherein said step (f) comprises providing a cyclic massage which includes shifting the weight of the animate object on said support surface so as to effectively move the part of the animate object on said structure.

14. The method defined in claim 1 wherein said step (a) comprises providing a wheel chair defining a configurable contoured seat and back areas.

15. The method defined in claim 1 wherein said step (a) comprises providing a bed defining a configurable support surface.

16. The method defined in claim 1 further comprising the step of:
   (g) wherein after step (f) is performed, at least one of steps (c), (d), (e) and (f) are repeated in accordance with a predetermined protocol.

17. The method defined in claim 16 wherein said step (g) comprises utilizing a predetermined protocol which is programmed into the processor by a user.

18. The method defined in claim 16 wherein said step (g) comprises repeating one of said steps based on time.

19. A device for supporting an animate object, comprising:
   a structure having a configurable contoured support surface;

a sensing device associated with said structure, said sensing device configured to measure an input parameter reflective of a pressure distribution of parts of the animate object contacting said structure;

a memory device for storing optimal comfort data and said pressure distributions determined by said sensing device;

a surface configuration device associated with said structure; and a processor associated with said sensing device, said memory and said surface configuration device, wherein said processor:

determines an optimal pressure distribution for the parts supported by said structure using a predetermined formula;

operates said surface configuration device so as to change a contour of said support surface so that the optimal pressure distribution is enacted on the parts; and operates the surface configuration device so as to periodically alter the configuration of the contoured surface in accordance with a predetermined protocol stored in said memory so that a cyclic massage is provided to the parts.

20. The device defined in claim 19 wherein said sensing device includes a plurality of fluid filled reservoirs at said support surface and at least one pressure detector operatively engageable with fluid in said reservoir.

21. The device defined in claim 20 wherein said configuration device includes means operatively connected to said reservoirs for modifying fluidic pressure in said reservoirs.

22. The device defined in claim 19 wherein said configuration device includes a plurality of fluid filled reservoirs at said support surface and means operatively connected to said reservoirs for modifying pressures of fluid in said reservoirs, thereby altering pressures exerted by said support surface on said body part.

23. The device defined in claim 19 wherein said support surface is a chair back and said measurement means includes means for monitoring biomechanical stress on a person's back.

24. The device defined in claim 19 wherein the predetermined protocol comprises a comparator circuit configured for comparing the measured input parameter with preset ranges of the input parameter, and wherein upon determining that the measured input parameter in a region of the support structure is outside of a respective preset range of the input parameter, said comparator circuit communicates with said surface configuration device initiating a massage cycle in the region.

25. The device defined in claim wherein said comparator circuit is incorporated in said processor.

26. The device defined in claim 19 wherein the predetermined protocol is programmed into said processor by a user.

27. The device defined in claim 19 wherein the predetermined protocol is based on time.

28. The device defined in claim 19 wherein the cyclic massage shifts the person's body parts on said structure so as to effectively move the person on the structure.

29. The device defined in claim 19 wherein the input parameter is taken from a group including pressure, temperature, mechanical shock, humidity, muscle tension, time and combinations thereof.

30. The device defined in claim 19 wherein said structure is a wheel chair.

31. The device defined in claim 19 wherein said structure is a bed.

32. The device defined in claim 19 further comprising a closed-loop feedback system such that after the cyclic massage is provided to the person=3 s body parts, the device continually repeats the procedure of measuring the input parameter, determining the optimal pressure distribution, changing the contour of the support surface, and providing the cyclic massage.

* * * * *